US00PP27077P3

(12) United States Plant Patent
Clark et al.

(10) Patent No.: US PP27,077 P3
(45) Date of Patent: Aug. 16, 2016

(54) ***COLEUS* PLANT NAMED 'UF09-8-37'**

(50) Latin Name: *Solenostemon scutellarioides*
Varietal Denomination: UF09-8-37

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 103 days.

(21) Appl. No.: 14/120,607

(22) Filed: Jun. 6, 2014

(65) Prior Publication Data

US 2015/0359157 P1 Dec. 10, 2015

(51) Int. Cl.
*A01H 5/12* (2006.01)

(52) U.S. Cl.
USPC ..... Plt./469

(58) Field of Classification Search
USPC ..... Plt./469, 373, 263.1
See application file for complete search history.

(56) References Cited

U.S. PATENT DOCUMENTS

PP21,585 P2 12/2010 Clark et al.
PP21,602 P2 12/2010 Clark et al.
PP23,585 P3 5/2013 Clark et al.

OTHER PUBLICATIONS

Buck. University of Florida IFAS News Feb. 19, 2014. UF/IFAS approves 14 new cultivars for release, retrieved on Nov. 9, 2015, retrieved from the Internet at <https://news.ifas.ufl.edu/2014/02/ufifas-approves-14-new-cultivars-for-release/> 4 pp.*

* cited by examiner

*Primary Examiner* — June Hwu
(74) *Attorney, Agent, or Firm* — Dentons US LLP

(57) ABSTRACT

'UF09-8-37' is a new coleus plant distinguished by having consistent lance shaped orange leaves, novel and vigorous growth habit, as disclosed herein.

3 Drawing Sheets

Latin name of the genus and species of the plant claimed: *Solenostemon scutellarioides.*

Cultivar denomination: 'UF09-8-37'.

BACKGROUND OF THE INVENTION

The invention relates to a new and distinct cultivar of coleus plant named 'UF09-8-37'. 'UF09-8-37' originated from an open pollination conducted in May-November 2008 in Gainesville, Fla. between the female coleus plant 'UF08-29-1' (unpatented) and an unknown male coleus plant. The first asexual reproduction was performed in May 2009 in Gainesville, Fla. by vegetative stem cuttings using a single seedling (see FIG. 1 for pedigree).

'UF09-8-37' has been reproduced asexually for over one year through vegetative stem cuttings and has been found to retain its distinctive characteristics through successive asexual propagations.

'UF09-8-37' has not been made publicly available more than one year prior to the filing date of this application.

When 'UF09-8-37' is compared to the female parent 'UF08-29-1' (unpatented), 'UF09-8-37' has deeply lobed, lance-shaped bronze/orange leaves and has a lateral spreading plant architecture. By contrast, 'UF08-29-1' is an upright, non-spreading plant with bronze-orange leaves that are serrated and typical of the species.

When 'UF09-8-37' is compared to the commercial cultivar 'Spitfire' 'UF07-24-5' (commercial, unpatented), both plants have lance-shaped, bronze-orange foliage, but leaves of 'UF09-8-37' are much larger in size and have deeper, more stable orange color in both sun and shade conditions. 'UF09-8-37' also has a more vigorous and more spreading growth habit with more lateral branching than 'Spitfire' 'UF07-24-5'.

SUMMARY OF THE INVENTION

The following are the most outstanding and distinguishing characteristics of 'UF09-8-37' when grown under normal horticultural practices in Gainesville, Fla. 'UF09-8-37' has a novel, vigorous, spreading growth habit, late season flowering, excellent heat tolerance, and consistent, lance-shaped orange leaves that are significantly different than other coleus plants. It has superior stability of foliage color in both sun and shade conditions, maintaining stable color in all conditions. It has a vigorous spreading growth habit with excellent lateral branching when grown as a stock plant, thus providing ample vegetative propagules for producers.

BRIEF DESCRIPTION OF THE DRAWINGS

This new coleus plant is illustrated by the accompanying photographs, which show the plant's form and foliage. The colors shown are as true as can be reasonably obtained by conventional photographic procedures.

FIG. 2—shows the growth habit, form, and foliage of the claimed plant.

FIG. 3—shows a close-up of the foliage.

DETAILED BOTANICAL DESCRIPTION

Figure 1:
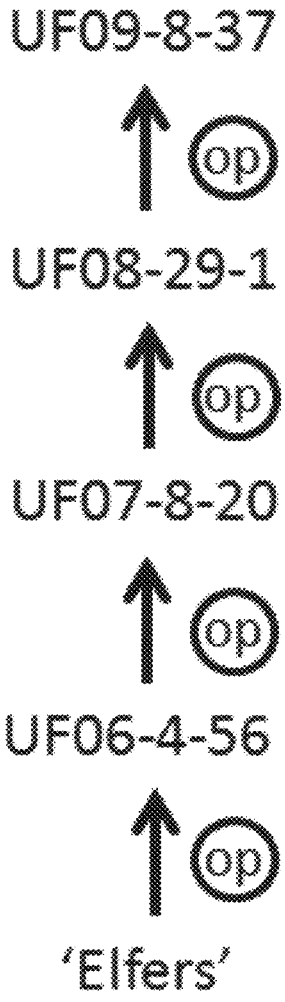
FIG. 1—shows the pedigree of the claimed plant.
Figure 2:
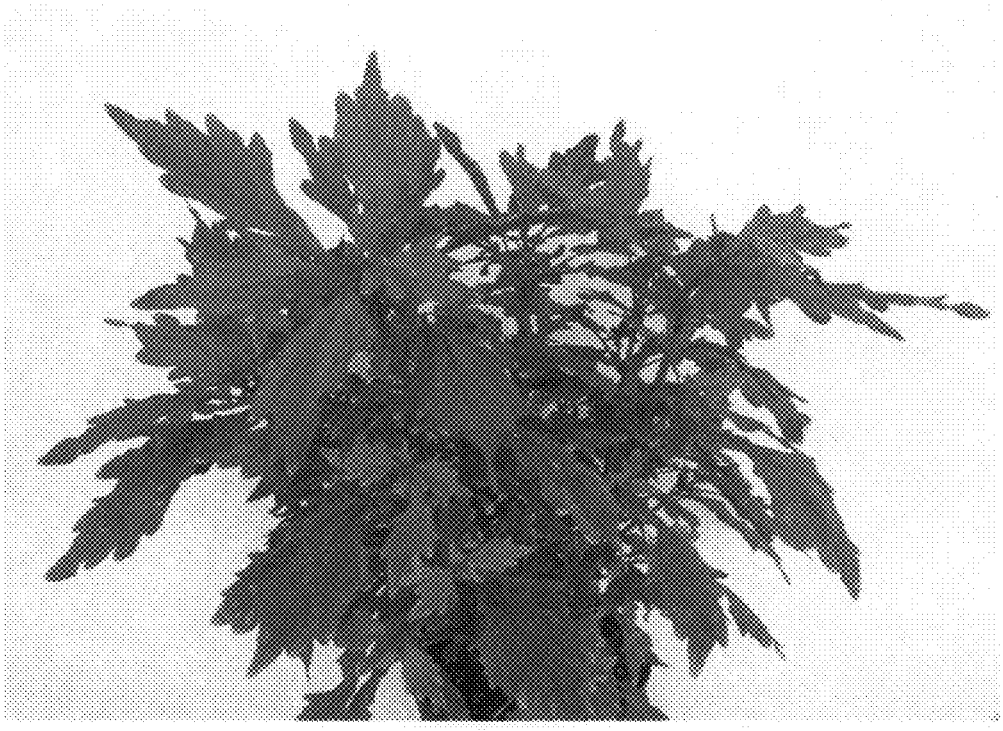
FIGS. 2 and 3 were taken of 9-week-old plants grown from cuttings in 1-gallon pots during September-November 2013 in greenhouses in Gainesville, Fla.
Figure 3:
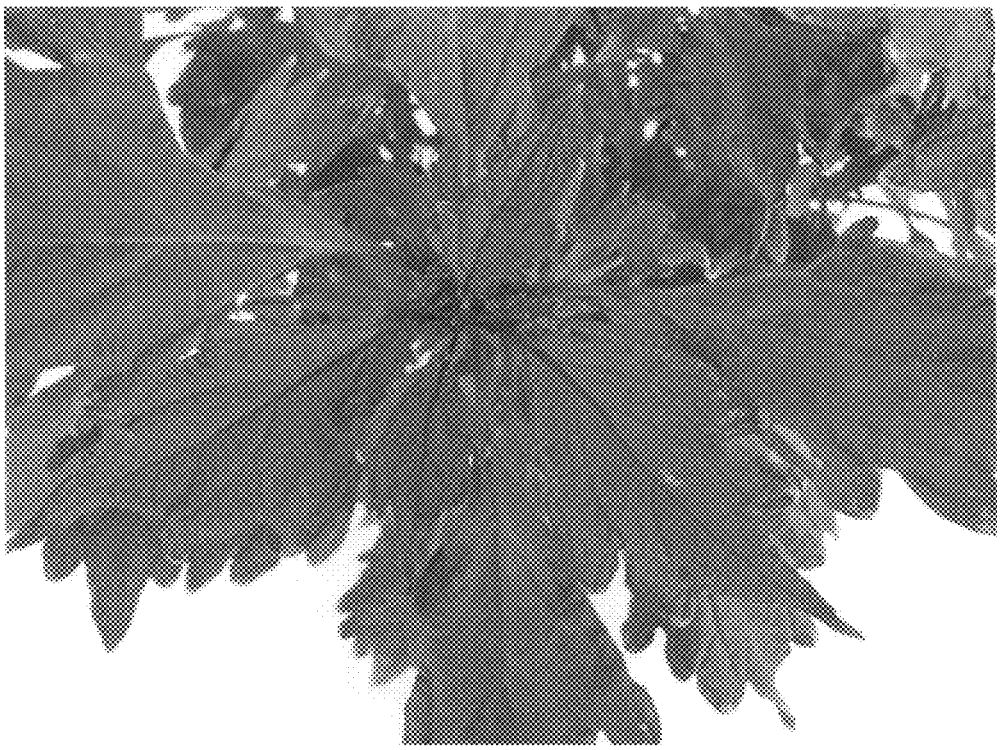

The following detailed description sets forth the distinctive characteristics of coleus variety 'UF09-8-37'. The detailed description was obtained using 9-week-old plants from cuttings growing in a glass greenhouse in Gainesville, Fla. in late fall 2013. The plants were pinched 2 weeks after cuttings were rooted, then grown in 1-gallon pots for approximately 9 weeks. Color references are to The R.H.S. Colour Chart of The Royal Horticultural Society of London (R.H.S.), 2007 5th Edition.

Classification:

*Family*.—Lamiaceae.

*Botanical*.—*Solenostemon scutellarioides*.

*Common name*.—Coleus.

*Cultivar name*.—'UF09-8-37'.

Parentage:

*Female parent*.—'UF08-29-1'.

*Male parent*.—Open-pollinated.

Plant description:

*Form*.—Spreading.

*Habit*.—Upright.

*Height* (*from top of soil*).—34-36 cm.

*Width* (*horizontal plant diameter*).—48-52 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—6 to 7 main branches per plant with numerous side branches, pinched once.

*Branch color*.—RHS 187A.

*Texture*.—Smooth.

*Pubescence*.—Non-descript.

*Stem description*.—Square-shaped stem, 1.5 cm in diameter at the soil line.

*Branch diameter*.—0.5-0.6 cm at the base of a 30-cm long branch.

*Branch length*.—30 cm.

*Internode length*.—3-5 cm.

*Anthocyanin*.—RHS 187A.

Leaves:

*Quantity of leaves per branch*.—16 to 18. Arrangement: Opposite.

*Fragrance*.—Not fragrant.

*Shape*.—Elliptic.

*Length*.—10-12 cm.

*Width*.—5-7 cm.

*Apex*.—Narrowly acuminate.

*Base*.—Oblique.

*Margin*.—Highly lobed.

*Leaf texture* (*both surfaces*).—Slightly pubescent upper surface; smooth lower surface.

*Pubescence color* (*both surfaces*).—Non-descript with naked eye.

*Venation color*.—Upper surface: RHS 187A. Lower surface: RHS 182B.

*Venation pattern*.—Upper surface: Reticulate. Lower surface: Reticulate.

*Color*.—Immature leaf: Upper surface: RHS N172B with leaf lobes and tips irregularly colored RHS N144B. Lower surface: RHS N186C.

*Color*.—Mature leaf: Upper surface: RHS N172B with leaf lobes and tips irregularly colored RHS N144B. Lower surface: RHS N186C.

*Petiole length*.—4-5 cm.

*Petiole diameter*.—0.2-0.3 cm.

*Petiole color*.—RHS 187B.

*Petiole texture*.—Smooth, no pubescence.

Flowers and seeds: Flowers and seeds have not been observed.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

What is claimed is:

1. A new and distinct variety of *Solenostemon scutellarioides* plant called 'UF09-8-37' as shown and described herein.

* * * * *